United States Patent [19]

Schlumberger et al.

[11] Patent Number: 4,899,318

[45] Date of Patent: Feb. 6, 1990

[54] METHOD AND DEVICE FOR RECONSTRUCTING THE SHAPE AND POSITION OF OBJECTS IN SPACE

[76] Inventors: Etienne Schlumberger, Tour Plein Ciel, 8 rue Emile Deslandres, Paris 75013; Maurice Schlumberger, Le Churut, 38700 Le Chappey en Chartreuse, both of France

[21] Appl. No.: 279,519

[22] Filed: Dec. 5, 1988

[30] Foreign Application Priority Data

Dec. 9, 1987 [FR] France ................... 8717140

[51] Int. Cl.⁴ .............................................. G03H 3/00
[52] U.S. Cl. .................................... 367/8; 364/413.25; 128/661.02; 367/119
[58] Field of Search ................ 367/7, 8, 88, 103–105, 367/138, 119, 120; 364/413.25; 128/660.06, 661.02

[56] References Cited

U.S. PATENT DOCUMENTS

| | | | |
|---|---|---|---|
| 4,105,018 | 8/1978 | Greenleaf et al. | 364/413.25 X |
| 4,495,816 | 1/1985 | Schlumberger | 128/661.02 X |
| 4,509,368 | 4/1985 | Whiting et al. | 128/661.01 X |
| 4,713,798 | 12/1987 | Kay | 367/7 X |

Primary Examiner—Thomas H. Tarcza
Assistant Examiner—Tod Swann
Attorney, Agent, or Firm—Kenyon & Kenyon

[57] ABSTRACT

The shape and position of objects in space can be reconstructed from at least two projections of these objects as obtained by transmission of waves influenced by their passage through said objects.

The method includes determining for each point of the projections the distance traversed through an object by each ray derived from each of the sources, in determining the volume which contains the object and the rays which are derived from the at least two sources and pass through said object, in plotting the distances traversed by the rays within the object from external limits of the volume containing the object to define a first space which is located within the object, then in plotting the distances from the external limits of the first space to define a second space which is necessarily located outside the object but within the initial volume, and so forth.

12 Claims, 6 Drawing Sheets

FIG_15a

FIG_15b

METHOD AND DEVICE FOR RECONSTRUCTING THE SHAPE AND POSITION OF OBJECTS IN SPACE

BACKGROUND OF THE INVENTION

1. Field of the Invention

The present invention relates to a method for reconstructing the shape and position of objects in three-dimensional space from at least two projections of said objects obtained by transmission of waves influenced by their passage through said objects from sources of said waves.

The term "object" is understood to mean a continuous ensemble which may or may not be a massive structure and which has essentially constant and homogenous physical characteristics such as, for example, blood vessels or bones in medical imaging or veins in geological formations.

The invention is also directed to a device for carrying out the method aforesaid.

2. Description of the Prior Art

The usual methods of locating an object in space are based on observation, from a number of different positions, of the external contours of the object to be defined and located.

The most common examples are directly derived from human stereoscopic vision. A similar approach is found in other fields such as geophysics or medicine irrespective of the waves employed, which range from electromagnetic radiation (x-rays, radar, standard vision) to sound waves (sonar, ultrasonic scanning). All these methods employ in all cases the abrupt differences of images (in attenuation or in reflection) for locating the contours of the object.

In order to locate an object with precision, these different methods make it necessary to surround the object with a sufficient number of observation points in order to define its contour. In the case of complex or irregular objects, this number can become very large, and the observation points must sometimes be so arranged as to surround the object completely, as in the case of a scanner, for example.

In the case of observations of "translucent" objects, in which the waves penetrate into the object without being totally absorbed, as in the case of x-ray images, an additional item of information appears in regard to the thickness of the object traversed. The attenuation is in fact a function of the coefficient of attenuation of the material traversed as well as the thickness of said material.

As indicated in the foregoing, the same situation occurs in the transmission of pressure waves such as seismic waves, for example. However, it is also possible in such a case to utilize the transit time aspects which also depend on the nature and thickness of the media being traversed.

In all cases, there therefore appears a relationship between the phenomenon observed and the distance traversed within the object.

If an object is subjected to waves which pass through it, and if the received waves are imaged, it is possible to obtain a map of the amplitude variation of said waves as a function, in particular, of the distance traversed by a ray within the object.

A well-known image of a map of this type is a radiograph. The lighter a point is on such a map, for example, the greater is the distance traversed by a ray within the object.

Any illuminating system in which there exists for each source only one ray which is clearly defined by its origin and its point of intersection with a known position on a photograph, and which passes through a point in space, will make it possible to establish a map of the modulation of the illuminating beam as a function of the distances traversed within the object.

Different types of projection naturally come to mind:
projections with parallel rays when the source is at infinity and when the receivers cover a reception plane,
conical projections when the source is at a finite distance,
more complex projections when the sources and the receivers are located on straight lines which are neither secant nor parallel, or else any other combination which makes it possible to "cover" a portion of space.

The most usual example of a conical projection is a radiographic image, or radiograph.

A single radiograph does not make it possible to reconstruct the spatial position of a given object although this radiograph offers much more information to its observer than a "photographic" image, in particular on the internal structure of the object in question.

Should it be desired to obtain more information on the interior of the object, it then becomes necessary to make a number of radiographs in accordance with a practice well known to radiologists. Sometimes, two radiographic images are not sufficient even for relatively simple objects, and it proves necessary in such cases to obtain a greater number from specific points.

Thus, in the case of a scanner, the entire circumference of an object is scanned. This involves making a very large number of projections of the object in order to reconstruct its shape and its position in space.

However, a scanner is an extremely complex and costly apparatus.

Attempts have been made to reconstruct an object from two projections (see Computer Vision, Graphics and Image Processing No. 3, Sept. 1984, A. Kuba). However, this method is applicable only to a limited number of cases.

SUMMARY OF THE INVENTION

The aim of the present invention is to provide a method which makes it possible to reconstruct the shape and position of objects in three-dimensional space from a very small number of projections (but at least two projections) and which can thus be simple and less costly than in the case of known methods which employ a very large number of projections.

In accordance with the invention, the method for reconstructing the shape and position of objects in space from at least two projections of these objects obtained by transmission from sources at spaced locations of waves that are modified by passage through said objects, comprises the steps of:

A/ determining in respect of each point of each projection the distance traversed through an object by each ray derived from the corresponding one of the sources, B/ determining a volume which contains the object as an envelope of all of the rays which are derived from the sources and pass through said object, C/ plotting the distances determined in step A from the external limits of the envelope determined in step B, D/ determining a first space in which the distances plotted in step C overlap; said first space being necessarily located inside the object, E/ plotting the distances determined in step A from the external limits of said first space as determined in step D, so as to define a second space, which is necessarily located outside the object and which is more restricted than the envelope determined in step B, and F/ repeating steps D and E with the successively determined inner and outer spaces so as to determine, by iteration, spaces which are located alternately outside and inside the object in increasing proximity to said object and thus progressively approach the shape and position of the object.

The distance traversed through an object can be determined for each projection by measuring, for example, the modification of the wave as it passes through the object.

The volume which is an envelope of all the rays which traverse said object can be determined with precision. This volume provides an approximate shape and position of the object.

The method in accordance with the invention makes it possible from a knowledge of the rays and of the distances traversed by said rays within the object, starting from the above-defined envelope, successively to determine spaces which necessarily are located alternately inside (step D) and outside (step E) the object.

The present applicants have established that, by repeating steps D and E several times, the difference between the space located inside the object and the space located outside the object becomes increasingly smaller and therefore these spaces increasingly approach the real contour of the object.

Thus, on condition that the positions and traversed distances of a large number of rays are accurately determined, it is possible to reconstruct the exact shape of the object from a small number of projections of said object. In simple cases, two projections may prove sufficient, but in more typical cases the method in accordance with the present invention utilizes at least three projections of the object. In such cases, the spaces which are located inside the object and the spaces which are located outside the object converge much more rapidly than in the case of two projections. In complex cases, a number of projections greater than three could be useful, as well as a judicious choice of positions of the sources and of the receivers.

In a preferred embodiment of the invention, other points of the object contour are determined from known points of said contour, such as the known points corresponding to the points of tangency to the object of planes containing two rays derived from two different sources, by plotting from the known points the distance traversed within said object by other rays which pass through said known points.

A knowledge of these points permits a better definition of the shape and position of the object. Thus, by utilizing these known points, the differences between the successive spaces determined by the method of the invention converge more rapidly.

The method in accordance with the invention can readily be applied to reconstruction of the shape and position of a plurality of adjacent objects.

To this end, the volume which contains each object and the rays which are derived from the sources and pass through said object are determined, and the shape and position of said object are determined from said volume as indicated earlier.

The aforesaid volume of each object is determined by the discontinuity in transmission of the rays when these latter reach the apparent contour of the object.

The method in accordance with the invention requires a large number of operations utilizing a large number of distances and rays which are determined with precision. However, this large number of operations can be performed by means of a computer of medium capacity.

According to another aspect of the invention, a device for carrying out the method of the invention includes means for obtaining at least two projections of an object by transmission of waves influenced by passage through said object from at least two sources of said waves, the device further comprising:

A/ means for determining in respect of each point of the at least two projections the distance traversed through the object by each ray derived from a corresponding one of the sources, B/ means for determining a volume which contains the object and all rays from the at least two sources which traverse said object, C/ means for determining points of tangency to the object of planes which contain two of the sources, D/ means for plotting the distances determined by means A from the external limits of the volume which contains the object as determined by means B, E/ means for determining a first space in which the distances plotted by means D overlap, said first space being located inside the object, F/ means for plotting the distances determined by means A from the external limits of the first space determined by means E to define a second space which is located outside the object and which is more restricted than the volume determined by means B, G/ means for repeating the operation of means D, E and F to determine successive spaces located alternately inside and outside the object in increasingly close proximity to said object.

The means B to G can be provided by an appropriately programmed computer. Thus the device in accordance with the invention comprises a system for obtaining at least two projections from a corresponding number of sources, means for measuring the distances traversed within the object by rays from each source, and a computer.

A device of this type is therefore simpler and should require less radiation than an apparatus, such as a scanner, for processing a very large number of projections.

DETAILED DESCRIPTION OF THE INVENTION

Figure 1:
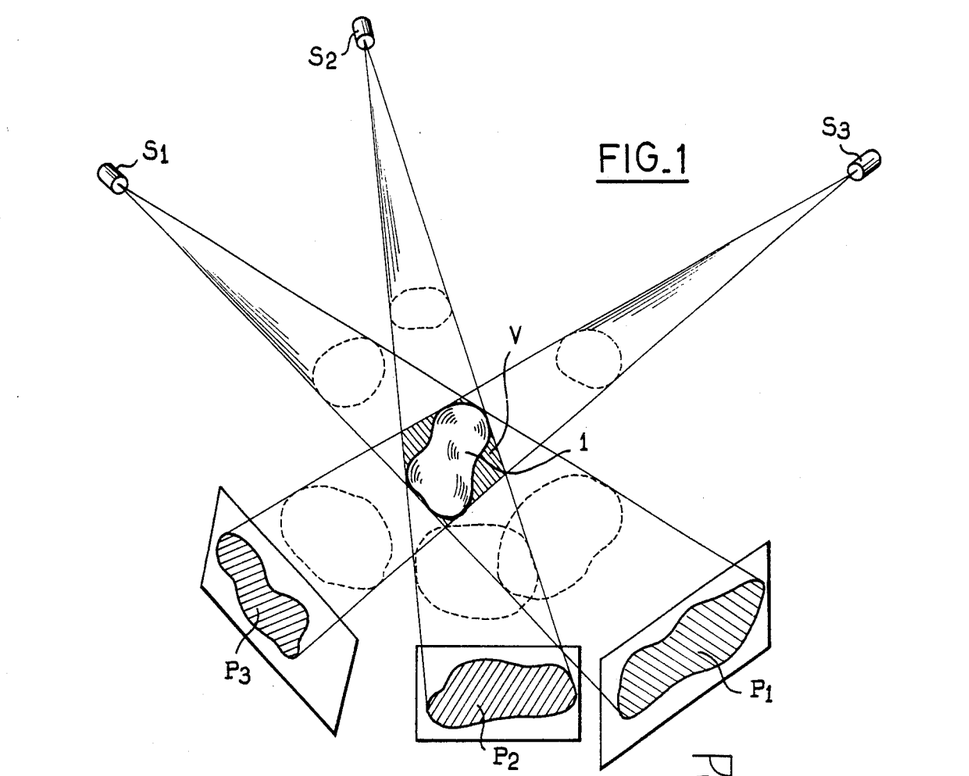
FIG. 1 is a schematic view showing an object and three projections of the object as obtained from three sources of waves which pass through said object.

In FIG. 1, the reference 1 designates an object having a shape and position in space which are desired to reconstruct in accordance with the method of the invention.

The references $P_1$, $P_2$, $P_3$ designate the projections of the object 1 obtained by transmission of waves influenced by their passage through said object from three sources $S_1$, $S_2$, $S_3$.

These waves can be x-rays or sound waves, for example. When they pass through the object 1, the waves undergo a modification which is a function of the distance traversed within said object.

By means of suitable sensors, it is therefore possible to determine in respect of each point of the projections $P_1$, $P_2$, $P_3$ the distance traversed through the object 1 by each ray derived from one of the sources $S_1$, $S_2$, $S_3$.

It is apparent from FIG. 1 that the object 1 is contained within a volume V which contains all the rays derived from the sources $S_1$, $S_2$, $S_3$ which pass through said object.

Determination of said volume V provides a first approximation of the shape and position of the object 1.

Figure 2:
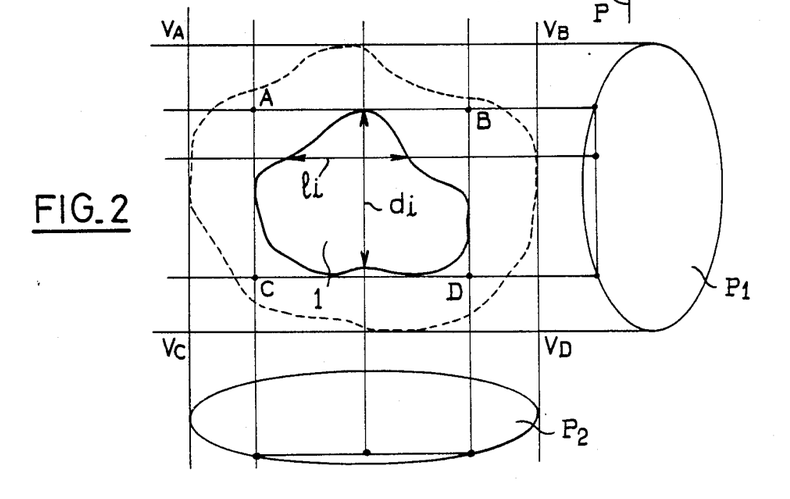
FIG. 2 is a schematic view showing an object, two projections of the object at right angles to each other and obtained from two sources of two mutually orthogonal sets of parallel waves, and a cross section of said object in a plane which intersects the sources.

In order to simplify the explanation of the method in accordance with the invention, it will be assumed that the object 1 is traversed solely by two perpendicular sets of parallel rays delivered by sources located at infinity or by two sets of point sources, each of which emits one set of parallel rays. This representation is shown in FIG. 2. The object 1 is contained within a volume which contains all the rays delivered by the sources and passing through said object, as represented schematically b $V_A$, $V_B$, $V_C$, $V_D$. The intersection of this volume with the plan P of FIG. 2 is a rectangle ABCD.

The simplified explanation describes the method for reconstructing the shape and position of the object 1 in the plane P of FIG. 2 within the rectangle ABCD. The reference $l_i$ designates the distance traversed within the object 1 by a ray which is parallel to AB or CD, and the reference $d_i$ designates the distance traversed by a ray which is parallel to AC or BD.

For the sake of simplification, the invention described hereinafter is illustrated by means of only two projections. Nevertheless, three projections or more are necessary in order to solve complex cases.

As already indicated in the foregoing, the rectangle ABCD surrounds the shape and position of the object 1 in the plane P. Moreover, it is possible to determine by scanning each point of the projections $P_1$, $P_2$ the distances $l_i$ and $d_i$ traversed within the object by the rays issuing from the sources.

Figure 3:
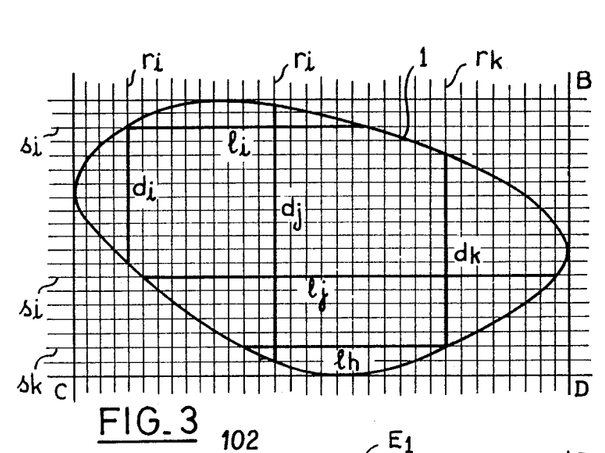
FIG. 3 is a sectional view of an object in a plane containing two perpendicular sets of parallel rays, bounded by the limit rays in this plane for which the distance traversed within the object is zero.

FIG. 3 shows a cross section of an object 1 contained within a rectangle ABCD. This object 1 is traversed by rays $r_i$, $r_j$, $r_k$ in the direction parallel to AC or BD and by rays $s_i$, $s_j$ and $r_k$ in the direction parallel to AB or CD.

The distances traversed by said rays are respectively $d_i$, $d_j$, $d_k$ in the case of $r_i$, $r_j$, and $r_k$ and $l_i$, $l_j$, $l_k$ in the case of $s_i$, $s_j$ and $s_k$.

Figure 4:
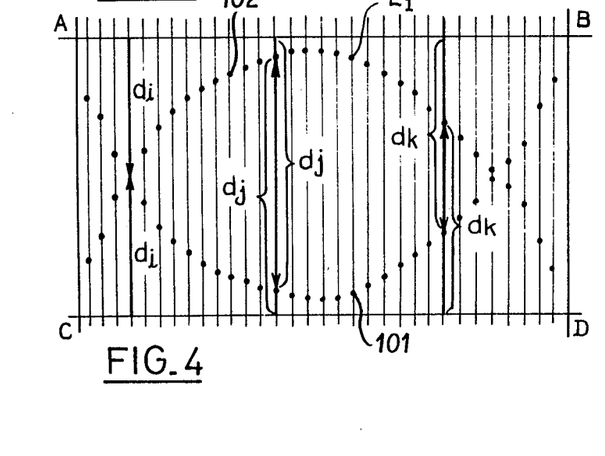
FIG. 4 is a view of a space inside the object obtained after plotting the distances traversed within said object by the first set of parallel rays from the limits of the containing area indicated in FIG. 3.
Figure 5:
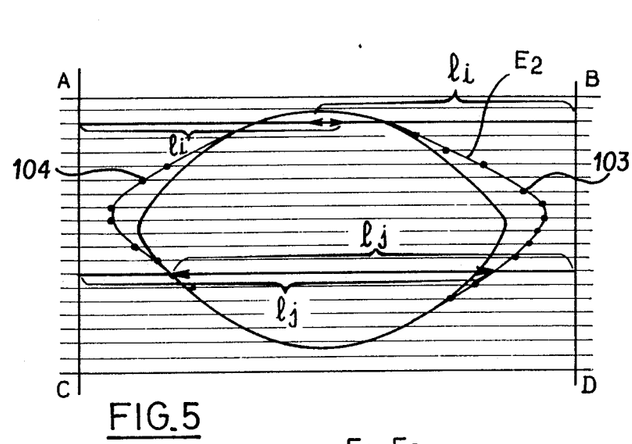
FIG. 5 is a view of a space inside the object obtained after plotting of the distances traversed within said object by the second set of parallel rays.

In the next step of the method, the distances traversed by the respective rays $d_n$ and $l_n$ within the object 1 are plotted from the opposite sides AB, CD and AC, BD of the quadrilateral ABCD which contains the object 1 in the case of two sources. That is, the distances $d_i$, $d_j$, $d_k$, etc. are plotted from line AB to produce a first set of points 101 (FIG. 4). The same distances are then plotted from line CD to produce a second set of points 102 (FIG. 4). In the same way, distances $l_i$, $l_j$, $l_k$, etc. are plotted both from lines AC and BD to produce the respective sets of points 103 and 104 (FIG. 5).

Thus, a closed space $E_1$ is obtained for the plots of distances $d_i$, $d_j$, $d_k$, etc. (see FIG. 4) and a closed space $E_2$ is obtained for the distances $l_i$, $l_j$, $l_k$, etc. (see FIG. 5). These spaces $E_1$ and $E_2$ correspond to areas where the respective plotted distances $d_n$ and $l_n$ overlap.

Figure 6:
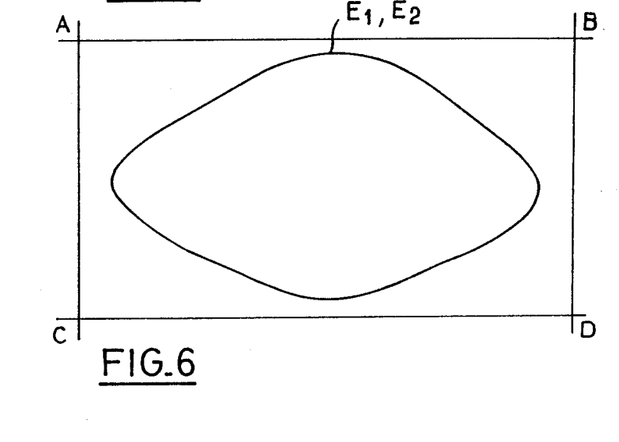
FIG. 6 is a view of a first space obtained by combining the distance plots of FIGS. 4 and 5.

By combining these two spaces, there is obtained a space $E_1$, $E_2$ (see FIG. 6) which is necessarily located within the interior of the object 1.

Figure 7:
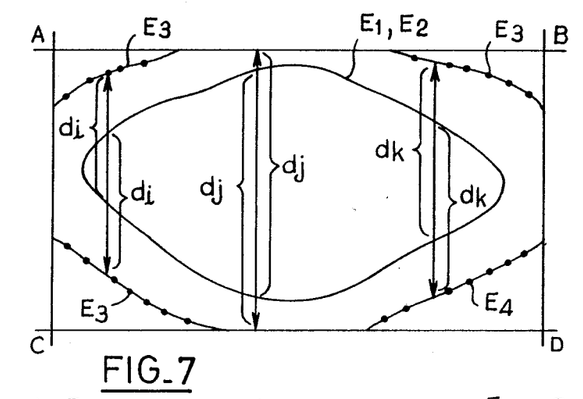
FIG. 7 is a view of a second space located outside the object obtained by plotting the distances traversed within said object by the first and second sets of rays from the internal first space of FIG. 6.

At this stage of the method, it is therefore known that the object 1 to be defined is located inside the quadrilateral ABCD and outside the space $E_1$, $E_2$. In a subsequent step of the method, the same distances $d_n$ and $l_n$ traversed by the rays within the object are plotted from the external limits of the necessarily internal space $E_1$, $E_2$ (see FIG. 7) to define a second space $E_3$ which is necessarily external to the object 1 yet which is contained within the quadrilateral ABCD.

The shape and position of the object 1 thereby have been defined with a higher degree of accuracy.

Figure 8:
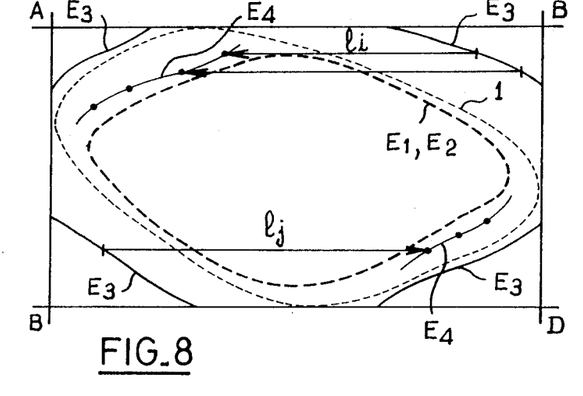
FIG. 8 is a view of a third space located inside the object and obtained from the external second space of FIG. 7.

In a subsequent step of the method, the distances $d_i$, $d_j$, etc. and $l_i$, $l_j$, etc. traversed within the object are plotted from the external limits of the aforesaid space $E_3$ (see FIG. 8) to define a third space $E_4$ which is necessarily located inside the object 1 but is outside the limits of the first space $E_1$, $E_2$. FIG. 8 therefore shows that a better definition of the shape and position of the object has again been achieved.

Starting from this new space $E_4$ which is internal to the object, a new space $E_5$ is determined as before by plotting the distances $d_i$, $d_j$, etc. and $l_i$, $l_k$, etc. (see FIG. 9). Said new space $E_5$ is necessarily external to the object 1 (as shown in dashed outline in FIGS. 8 and 9) and is within the previously defined space $E_3$ which is external to the object.

Figure 9:
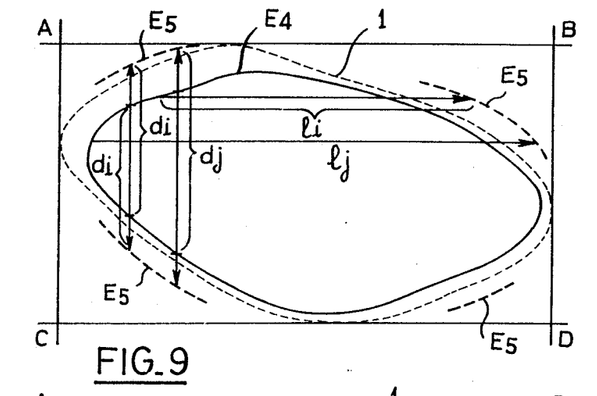
FIG. 9 is a view of a fourth space located outside the object and obtained from the internal third space of FIG. 8.

It is apparent from FIG. 9 that the difference between the internal and external spaces $E_4$ and $E_5$ has been reduced still further.

The preceding steps are then repeated in order to determine by iteration spaces which are located outside and inside the object 1 in increasing proximity to the actual outline of said object. The result thus achieved is to determine the position and the shape of the object 1 to any desired accuracy within the quadrilateral ABCD.

Moreover, the convergence of the differences between alternate internal and external spaces is even more rapid in the case in which more than two sources are employed.

It will readily be apparent that, in the case of point sources which emit conical beams, the process which has just been explained is exactly the same.

Figure 10:
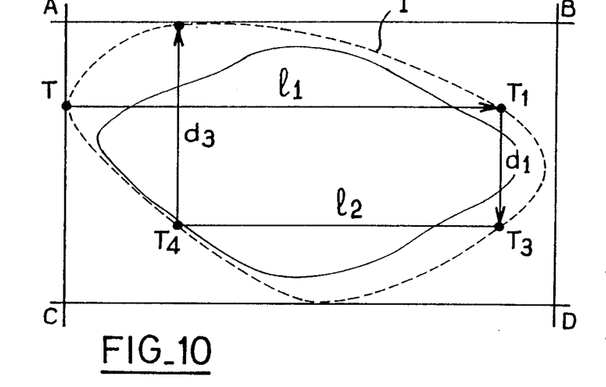
FIG. 10 is a view showing initial steps of the method for determining successive new points from a known point by plotting the distances traversed within the object in successive perpendicular directions.

In order to increase the speed of convergence of the differences between the spaces located outside and inside the object, it is an advantage to start with known points on the outline of the object. These known points may correspond to the points of tangency to the object of planes containing two rays, for example at the point T in FIG. 10, issuing from two different sources. In the case of three or more projections, at least three rays pass through such a point T, two of which are tangent to the object.

By plotting from said point T the distance $l_1$ traversed within the object 1 by a ray from another source which passes through said point T, a second known point $T_1$ is determined within the limit of accuracy of measurements. This second known point $T_1$ makes it possible to determine, by plotting the distance $d_1$ from one source, a third point $T_3$, then a fourth point $T_4$ by plotting of $l_2$ from the other source, then a fifth point by plotting $d_3$ from the one source, and so on.

By virtue of these known points of the object, enhanced accuracy is achieved in defining the spaces between which the object 1 is located.

Figure 12:
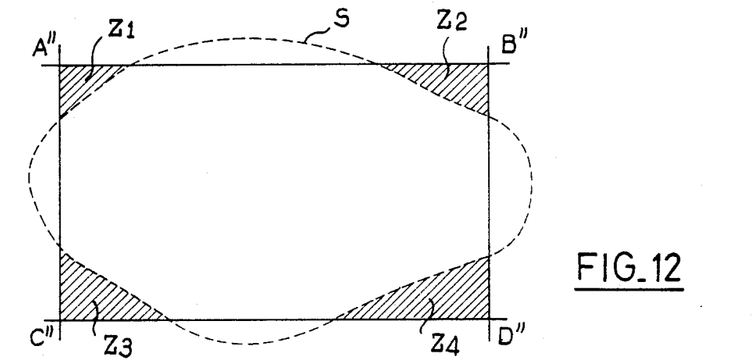
FIG. 12 is a diagram illustrating use of the apparent contour in the case of a third projection.

When more than two projections are employed, as illustrated in FIG. 1, the cross section of the volume V containing the object 1 appears in the form of a polygon A"B"C"D" (see FIG. 12) (corresponding to the first two projections) on which is superimposed the cross section in dashed lines, of the surface of apparent contour S of the third projection. As indicated in FIG. 12, this superposition results in exclusion zones $Z_1$, $Z_2$, $Z_3$, $Z_4$ which are external to the object, thus making it possible to begin the method on the basis of a volume containing the object which is more accurate than the quadrilateral A"B"C"D".

The method which has just been described can also be applied to reconstruct the shape and position of a plurality of adjacent objects or objects contained within each other.

Figure 11:
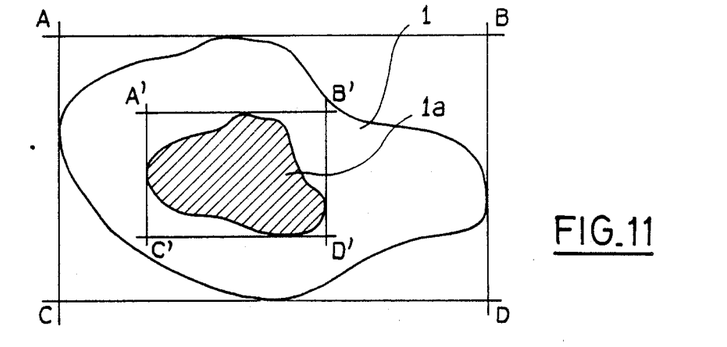
FIG. 11 is a diagram illustrating the method of reconstruction of an object contained within another object.

Thus FIG. 11 represents a smaller object $1a$ contained within a larger object.

In this case, the initial step comprises determining the volume (or the area of the rectangle A'B'C'D' in the simplified two source example shown) which contains the object $1a$ and the rays which are derived from the sources and pass through said object $1a$.

Said volume (or rectangle A'B'C'D') can be determined by the discontinuity in transmission of the rays when these latter reach the apparent contour of the object $1a$.

Once the volume containing the object $1a$ is determined, this latter is subtracted from the object 1 as a whole so as to determine the shape and position of the object $1a$, by applying the method in accordance with the object $1a$. This subtraction can be performed by providing the volume of the object $1a$ with the same characteristics as those of the object 1. Since the shape and position of the object 1 are known with precision, the shape and position of the object $1a$ can be accurately determined by applying the method described in the foregoing.

In practice, the plots of the distances $d_i$, $d_j$, $d_k$, etc. and $l_i$, $l_j$, $l_k$, etc. for determining the spaces located inside and outside the object in increasingly greater proximity thereto can be performed by means of a computer which is capable of carrying out a large number of operations in a short time.

The precision of determining the positions and shapes of objects depends essentially on the number and position of the different rays, on the accuracy with which they are located, as well as the accuracy of determination of the distances traversed within the object. This accuracy of location and of distances traversed can be considerably facilitated by incorporating markers of known arrangement and position in the space to be scanned. Thus a set of four markers defining a reference sphere can be particularly suitable.

Figure 13:
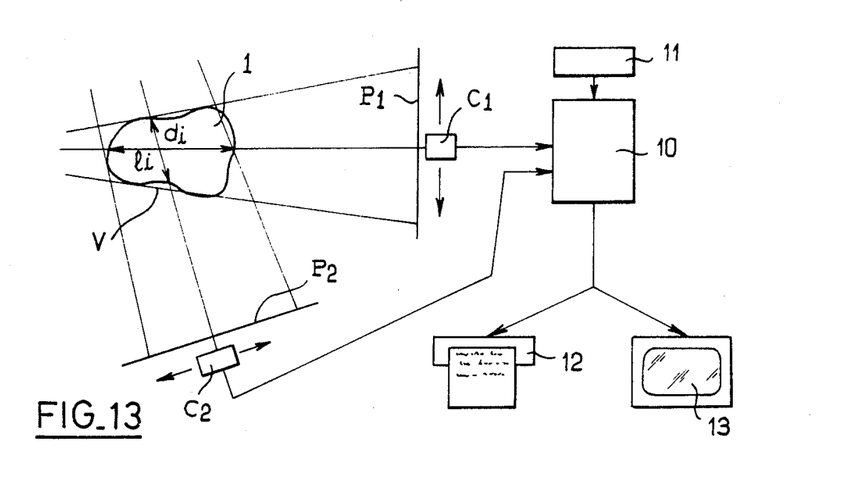
FIG. 13 is a schematic diagram of a device in accordance with the invention.

A device for the practical application of the method in accordance with the invention is illustrated schematically in FIG. 13.

This device comprises sensors $C_1$, $C_2$ which are capable of measuring the intensity of rays which have passed through the object 1 at each point of the projections $P_1$ and $P_2$.

A computer 10, which is connected to said sensors $C_1$, $C_2$, is capable of converting these intensities to distances traversed within the object 1.

The computer 10 is also programmed to determine the position of each ray and the initial volume V which contains the object 1 and all the rays which pass through the object 1. Said computer 10 is provided with an input means 11 for introducing the initial data of the device into the memory of said computer.

Said computer 10 is also connected to a printer 12, on which are printed the results of calculations, and to a display screen 13, on which there can be shown the final shape of the object as well as its approximate shape at any predetermined stage of calculations.

It can readily be understood that the computer 10 will be able on demand to reconstruct any cross section of the object on the printer 12 or the screen 13.

A logic system simulating the method of reconstruction in accordance with he invention has been developed to compare the performances of different algorithms which can be employed for the practical application of said method.

The object of this logic system is to reconstruct the shape of a three-dimensional object from calculated digitized radiographic views obtained from an initial three-dimensional model of the object. In this logic system, the preliminary step of actually radiographing the object is replaced by a set of simulated x-ray projections, by way of example.

Figure 14:
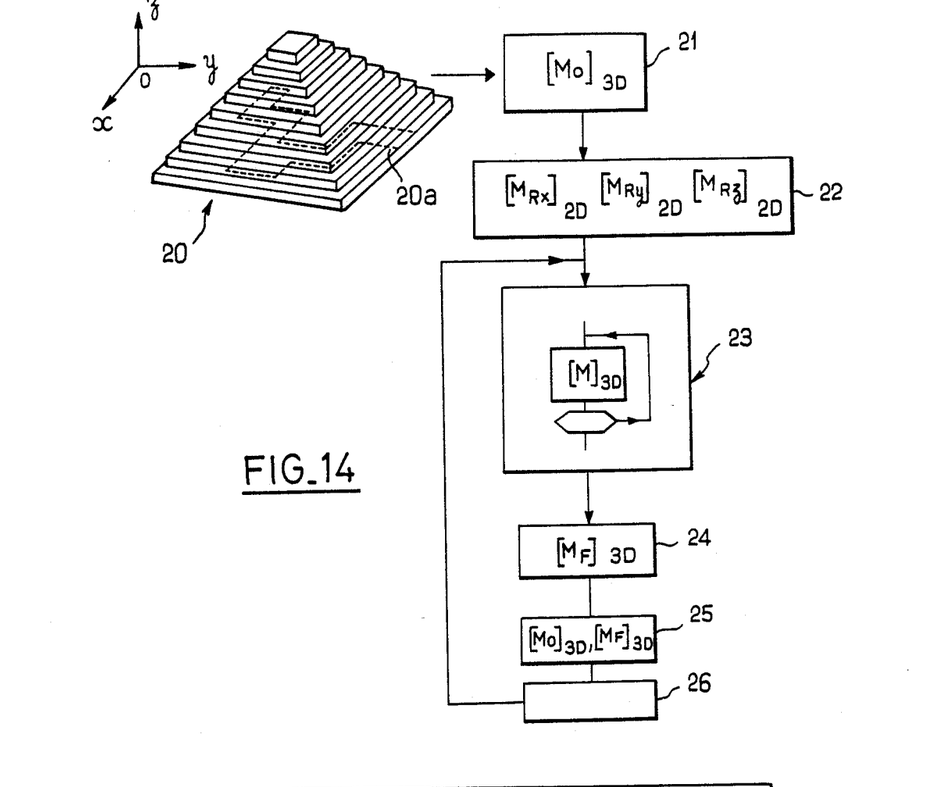
FIG. 14 is a flow diagram illustrating the principal steps of the logic system in a test simulation of the method in accordance with the invention.

The object whose reconstruction is to be simulated, for example a hollow pyramid 20 having a labyrinth $20a$ as shown in FIG. 14, is modeled in the form of a three-dimensional reference matrix 3D during a modeling step 21. From this reference matrix are generated three two-dimensional matrices $[Mrx]_{2D}$, $[Mry]_{2D}$ and $[Mrz]_{2D}$, respectively equivalent to three radiographic views of the object which would have been taken along the axes Ox, Oy and Oz (step 22). These three matrices then constitute the basic data which are necessary for the resolution step 23 corresponding to the method in accordance with the invention. This resolution step utilizes an algorithm operating on a calculation matrix $[M]_{3D}$ and iterated a variable number of times until there is obtained a reconstruction matrix $[M_F]_{3D}$ of the object concerned (step 24). The reconstruction matrix $[M_F]_{3D}$ is then compared (step 25) with the reference matrix $[M_o]_{3D}$ from which the three simulated radiographic views originated. The performances of the algorithms employed can be determined from the result of this comparison Thus a number of algorithms utilizing deductive or probabilistic methods have been successfully tested.

The simulation logic system developed for this purpose is endowed with numerous functionalities which make it possible to display the reconstruction of the object during the different steps of the method, to modify the initial conditions, to carry out numerous operations on the matrices employed in the logic system and to identify after comparison any possible errors of reconstruction.

Figure 15A:
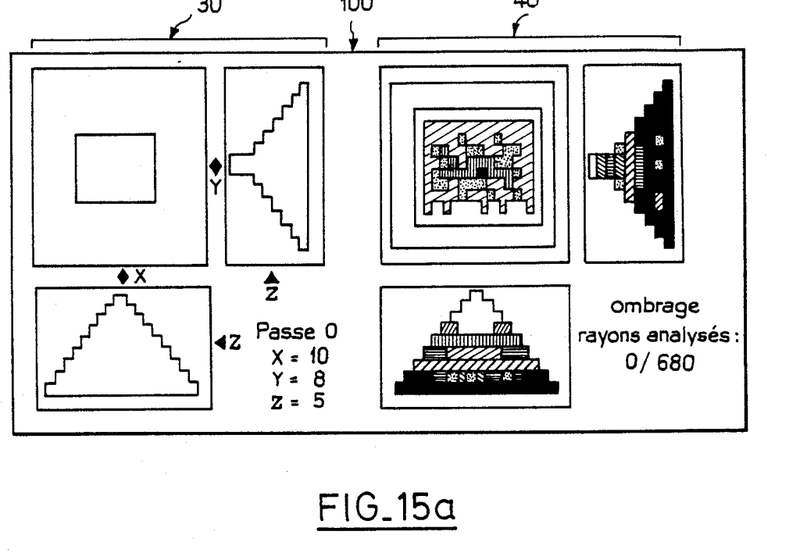
FIG. 15a, 15b and 15c are views of screen images obtained with the simulation logic system of FIG. 14.
Figure 15B:
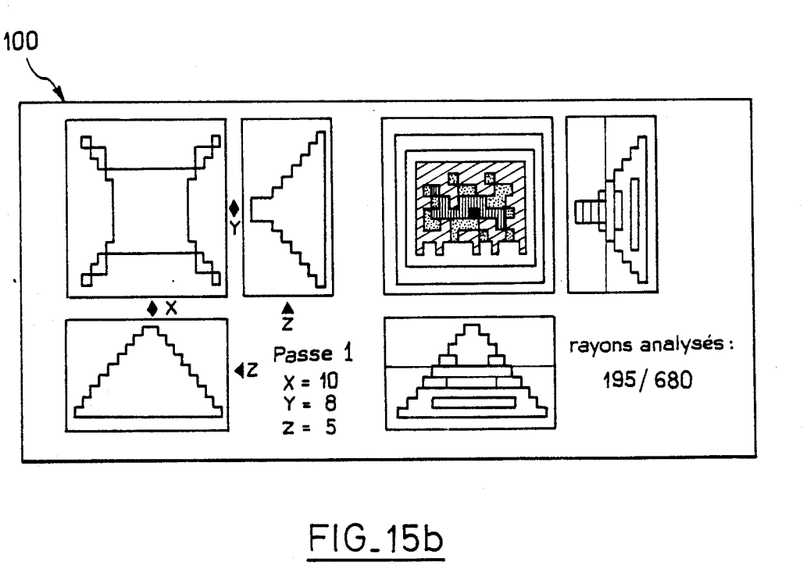
Figure 15C:
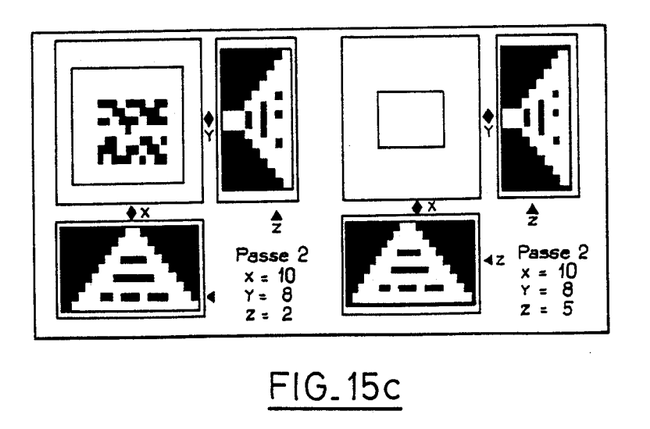

Written for use in interactive form on a microcomputer, said simulation logic system of the method in accordance with the invention provides the user with screen images such as those shown in a highly simplified manner in FIG. 15. The left-hand portion 30 of the screen 100 represents three cross sections, according to predetermined values of x, y and z, of the image during reconstruction of the object under study, namely in the present case a hollow pyramid having a labyrinth. It is possible by means of suitable controls to move within the image.

The right-hand portion 40 of the screen 100 comprises the three radiographic views taken along the three axes Ox, Oy and Oz obtained by simulation of an x-ray generator on the three-dimensional reference matrix $[Mo]_{3D}$. With each elementary cell of a radiographic view there is an associated grey density corresponding to the equivalent penetration of a ray through the object at the location of the cell concerned.

FIG. 15a illustrates a screen image obtained at the time of an initial stage of execution of the simulation logic system, known as shadowing, during which the elementary cells corresponding to zero densities of materials are detected and localized, thus making it possible to define the external contours of the object. FIG. 15b corresponds to a temporary display of the reconstructed image at a given instant during a first resolution pass, when only 195 rays out of 680 have been scanned. On completion of a second pass and after scanning of all the rays which pass through the different cells of the object, there is obtained a final reconstructed image of the hollow pyramid, with reference to FIG. 15c which shows by way of example the three cross sections of the reconstructed image along (x,y,z)=(10, 8, 5) and (x,y,z)=(10,8,2). At this stage of execution of the logic system, it is wholly possible to scan the entire three-dimensional image thus obtained and to compare it with the reference three-dimensional image.

It is worthy of note that the screen images generated by this simulation logic system show other windows and in particular control windows which are not illustrated in FIGS. 15a to 15c.

It should be clearly understood that the invention is not limited to the examples of execution described in the foregoing and that a large number of modifications may be made in these examples without thereby departing either from the scope or the spirit of the invention. In particular, it would be possible to reconstitute markers having well-defined positions and arrangements so as to permit more accurate position-location of the different rays.

What is claimed is:

1. A method for reconstructing the shape and position of objects in space from at least two projections of these objects obtained by transmission from sources at spaced locations of waves that are modified by passage through said objects, wherein said method comprises the steps of:
   (a) determining in respect of each point of each projection the distance traversed through an object by each ray derived from a corresponding one of the sources,
   (b) determining a volume which contains the object, the volume comprising an envelope of all the rays which are derived from the sources and pass through said object,
   (c) plotting the distances determined in step (a) from the external limits of the envelope determined in step B,
   (d) determining a first space in which the distances plotted in step (c) overlap, said first space being necessarily located inside the object,
   (e) plotting the distances determined in step (a) from the external limits of the first space as determined in step (d) so as define a second space, which is necessarily located outside the object and which is more restricted than the envelope determined in step (b),
   (f) repeating steps (d) and (e) with the successively determined inner and outer spaces so as to determined, by iteration spaces which are located alternately outside and inside the object in increasing proximity to said object and thus progressively approach the shape and position of the object.

2. A method according to claim 1, wherein other points of the object contour are determined from known points of said contour corresponding to points of tangency to the object of planes containing two rays derived from two different ones of said sources, by plotting from the known points the distance traversed within said object by other rays which pass through said known points.

3. A method according to claim 2, wherein the other points thus determined increase the precision of the spaces between which the object is located.

4. A method according to claim 1 as applied to reconstruction of the shape and position of a plurality of objects which may or may not be separate, wherein the volume which contains each object and the rays which are derived from the sources and pass through said object are determined and the shape and position of said object are determined from said volume as determined in step (b).

5. A method according to claim 4, wherein the volume of each object is determined by the discontinuity in transmission of the rays when these latter reach the contour of the object.

6. A method according to claim 5, wherein the volume containing a particular object is subtracted from the volume as determined in step (b) in order to determine successively the shape and position of the other objects.

7. A method according to claim 1, wherein said method is carried out by means of a computer.

8. A device for reconstructing the shape and position of objects in space comprising means for obtaining at least two projections of said objects by transmission of waves influenced by passage through said objects from at least two sources of said waves, wherein said device further comprises:

- A means for determining in respect of each point of the at least two projections the distance traversed through the objects by each ray derived from a corresponding one of the sources,
- B means for determining a volume which contains the object and all rays from the at least two sources which traverse said object,
- C means for determining points of tangency to the object of planes which contain two of the sources,
- D means for plotting the distances determined by means A from the external limits of the volume which contains the object determined by means B,
- E means for determining a first space in which the distances plotted by means D overlap, said first space necessarily being located inside the object,
- F means for plotting the distances determined by means A from the external limits of the first space determined by means E to define a second space which is necessarily located outside the object and which is more restricted than the volume determined by means B,
- G means for repeating the operation of means D, E, and F to determine successive spaces located alternately inside and outside the object in increasingly close proximity to said object.

9. A device according to claim 8, wherein means B through G comprise a computer having stored in a memory, in respect of each point of the projections, the distance traversed through an object by each ray derived from a corresponding one of the sources, the position and shape of the volume which contains the object, and the rays derived from the two sources which pass through said object, the computer being programmed for calculating the points of intersection between the rays and said volume, for plotting said distances from said points of intersection, for calculating the positions obtained after said plot, and then successively plotting the distances from these new positions, until the differences between the calculated new positions are within a preselected value to the positions calculated in the preceding cycle.

10. A device according to claim 9, wherein the computer is programmed for determining the shape and position of a crosssection of the object in any plane of said object.

11. A device according to claim 10, wherein the computer is associated with means for displaying the result of its calculations.

12. A device according to any one of claims 8 to 11, wherein said device comprises markers having a predetermined arrangement and position in the space containing the objects to be located.

* * * * *